(12) United States Patent
Shalaby

(10) Patent No.: US 6,299,631 B1
(45) Date of Patent: Oct. 9, 2001

(54) POLYESTER/CYANOACRYLATE TISSUE ADHESIVE FORMULATIONS

(75) Inventor: Shalaby W. Shalaby, Anderson, SC (US)

(73) Assignee: Poly-Med, Inc., Pendleton, SC (US)

(*) Notice: Subject to any disclaimer, the term of this patent is extended or adjusted under 35 U.S.C. 154(b) by 0 days.

(21) Appl. No.: 09/439,167

(22) Filed: Nov. 12, 1999

Related U.S. Application Data

(60) Provisional application No. 60/115,836, filed on Jan. 14, 1999, and provisional application No. 60/102,868, filed on Nov. 12, 1998.

(51) Int. Cl.$^7$ .................................................. A61B 17/08
(52) U.S. Cl. ............................................................ 606/214
(58) Field of Search .................................. 606/213, 214; 524/460, 461; 526/298

(56) References Cited

U.S. PATENT DOCUMENTS

| | | | |
|---|---|---|---|
| 3,221,745 | 12/1965 | Coover, Jr. et al. | 128/334 |
| 3,223,083 | 12/1965 | Cobey | 128/92 |
| 3,264,249 | 8/1966 | Araki et al. | 260/32.4 |
| 3,559,652 | * 2/1971 | Banitt et al. | 606/214 |
| 5,350,798 | * 9/1994 | Linden et al. | 525/41 |
| 5,612,052 | 3/1997 | Shalaby | 426/426 |
| 5,653,730 | * 8/1997 | Hammerslag | 606/213 |

OTHER PUBLICATIONS

Shalaby, *Biabsorbable Polymers*, Encyclopedia of Pharmaceutical Technology, vol. 1, Marcel Dekker, Inc., New York and Basel, 1988, pp. 465–476.

* cited by examiner

Primary Examiner—Gary Jackson
(74) Attorney, Agent, or Firm—Leigh P. Gregory

(57) ABSTRACT

The present invention is directed to bioabsorbable adhesive/hemostatic formulations of a 2-alkoxyalkylcyanoacrylate and liquid or solid polymeric modifiers and adjuvant. The present adhesive formulations are useful as tissue adhesive/sealants, hemostatic agents, and as a means for patching or anastomic coupling of damaged organs.

4 Claims, No Drawings

POLYESTER/CYANOACRYLATE TISSUE ADHESIVE FORMULATIONS

This appln claims benefit of Prov. Nos. 60/102,868 filed Nov. 12, 1998 and 60/115,836 filed Jan. 14, 1999.

BACKGROUND OF THE INVENTION

For many years, surgical tissue closure has been accomplished by a variety of fundamental techniques such as the use of clamps, staples, or a variety of sutures. Disadvantages associated with use of those techniques in certain situations has led to the development of new techniques for joining damaged mammalian tissues and reducing or preventing the loss of blood or other bodily fluids as well.

One approach has been the development of tissue adhesives for joining tissues, derived from either natural or synthetic products. Adhesive bonding with natural products such as fibrin or glues derived from mollusks such as mussels and barnacles has shown promise. Fibrin glue has been prepared by reacting a cryoprecipitate of fibrinogen and thrombin in the presence of a calcium ion to produce fibrin monomer. This monomer reacts in the presence of a factor found in the patient's blood (Factor XIII) to form a polymer. These fibrin glues have found use in topical and spray applications as a hemostatic agent on bleeding anastomoses, bleed points caused by needle holes or suture lines, and on the heart surface to control bleeding. The fibrin glues have only a modest tensile strength and therefore have not found significant use for repairing tissues which are subjected to moderate or high stresses, and particularly cyclic ones.

Barnacle glue has shown promise since its polymerization is rapid and occurs under conditions which are similar to the environment in which they would be used. It also maintains its adhesive properties under adverse chemical conditions. However, under typical use conditions, the resulting adhesive joint has unacceptable tensile strength. Preparation of glues from mollusks is difficult, however, and large quantities of material must be processed to obtain a significant amount of adhesive. To prepare 1 milligram of adhesive from barnacles requires the harvest and treatment of at least 150 barnacles.

For these reasons, a great deal of attention has been given to the development of synthetic adhesive systems. Especially prominent has been the development of adhesive and hemostasis-inducing compositions comprising fast curing monomers such as dialkyl methylene malonates (U.S. Pat. No. 3,221,745) and monomeric lower alkyl 2-cyanoacrylates (U.S. Pat. Nos. 3,223,083 and 3,264,249). Because the lower alkyl 2-cyanoacrylates did not appear to combine the desired, if not the necessary, properties of low toxicity and adequate adsorption by tissues, the use of alkoxyalkyl 2-cyanoacrylate was developed (U.S. Pat. No. 3,559,652). Other polymers presently under investigation as tissue adhesives include polyurethanes and epoxy resins. The latter two polymer systems suffer disadvantages of having limited "pot life" or "open time," exhibiting significant exothermic reaction when polymerized (or cured) and being toxic to surrounding tissues.

It is advantageous for tissue adhesives to capable of being absorbed or degraded in the body, otherwise described as bioabsorbable or biodegradable. Secondly, it is obviously desirable that a device used in vivo should only remain as long as necessary to insure proper healing. This should reduce or prevent adverse tissue reactions and foreign body responses. In orthopedic applications, absorbable pins and plates that could perform in place of metal implants would require only a single surgical procedure. Absorbable polymers would also be useful for use with implantable systems for long-term drug delivery.

Shalaby in *Encyclopedia of Pharmaceutical Technology*, Swarbrick and Boylan, Eds., Marcel Dekker, Inc., New York, 1988, pp. 465–476, has classified bioabsorbable polymers into three groups: soluble, solubilizable, and depolymerizable. Soluble polymers are water-soluble and have hydrogen-bonding polar groups, the solubility being determined by the type and frequency of the polar group(s). Solubilizable polymers are usually insoluble salts such as calcium or magnesium salts of carboxylic or sulfonic acid-functional materials which can dissolve by cation exchange with monovalent metal salts. Depolymerizable systems have chains that dissociate to simple organic compounds in vivo under the influence of enzymes or chemical catalysis.

The response of tissues to biodegradable materials is dependent on the rate of absorption, but more importantly, it is regulated by the toxicity of the degradation products. Thus, it is important to have controlled absorption to decrease the toxicity and reaction of surrounding tissue to products that do elicit a response. It also is important to ensure that the mechanical properties of the polymer are maintained for sufficient time to allow proper healing. Thus, absorbable polymeric adhesives and the products of their bioabsorption must be compatible with the surrounding tissues.

2-Cyanoacrylates bond rapidly to tissues and form strong adhesive joints. Their properties may be modulated by varying their substituent groups. They are well-suited for biological applications since, unlike other adhesives such as epoxy resins and polyurethanes, 2-cyanoacrylates may be used as pure monofunctional monomers having well-defined properties. They homopolymerize rapidly at room temperature in the presence of weakly basic moieties such as water and other weakly basic species present in body fluids. Since their introduction in 1958, they have found use in many surgical applications such as hemostasis, as sealants for retrofilling, and as general tissue adhesives. A 2-cyanoacrylate suitable for use as a tissue adhesive should be non-toxic and biodegradable, should wet and spread on tissue substrates, and polymerize quickly to a thin, polymeric film. The polymeric adhesive should have a degree of flexibility, especially when bonding soft tissues. Biodegradability is especially important because the adhesive should be replaced by natural tissues and not slow or bar complete healing.

In the homologous series of poly(alkyl 2-cyanoacrylates) the lower homologs such as the methyl ester exhibit the highest rate of bioabsorption but also elicit the greatest tissue response. They also do not wet, spread or polymerize on biological substrates as rapidly as the higher homologs. On the other hand, the higher alkyl esters, such as the isobutyl, n-butyl or octyl ester, elicit relatively less tissue reaction but degrade too slowly, if at all. Therefore, the main drawbacks for use of the alkyl 2-cyanoacrylates has been their lack of practical biodegradability. Accordingly, Linden and Shalaby [U.S. Pat. No. 5,350,798 (1994)] developed an absorbable tissue adhesive formulation that is based on 2-cyanoacrylate and biocompatible oxalate polymers as reactive plasticizers and thickening agents to allow modulus matching of the adhesive and substrate. More specifically, the Linden/Shalaby system comprises at least one 2-cyanoacrylate ester of the general formula (I).

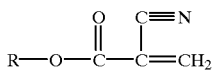

(I)

wherein R is selected from the group consisting of alkyl groups having from 1 to about 8 carbon atoms and, preferably, alkoxyalkyl groups having the formula $R_1$—O—$R_2$—wherein $R_1$ is an alkyl group having from 1 to about 8, preferably 2 to 3 carbon atoms and $R_2$ is an alkylene group having from 3 to about 6, preferably 3 to 4 carbon at 5, in an admixture with from about 2 percent to about 25 percent, preferably about 5 to 10 percent, of at least one oxalic acid polymer of the general formula (II)

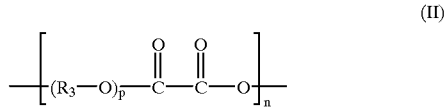

(II)

wherein each $R_3$ is an alkylene group having from 2 to about 4 carbon atoms, each p is an integer from 1 to about 4, with the proviso that not more than about 1 of each 20 p's is 1, and n is the degree of polymerization which results in a polymer which does not initiate polymerization upon mixing with the 2-cyanoacrylate monomer and standing for about 12 hours. Suitable alkylene groups include but are not limited to ethylene, propylene, trimethylene, butylene, isobutylene, and tetramethylene. It is preferred that p have a value of 3 and $R_3$ is ethylene. Where p is 1 it is preferred that $R_3$ is trimethylene.

However, the Linden/Shalaby systems are limited to compliant absorbable oxalate-based copolyesters having short polyalkylene oxide segments (p=1–4) which limit the broad utilization of the cyanoacrylate as tissue adhesives for adjoining or sealing tissues where the adhesive is required to have a modulated absorption profile or absorbs over a longer period of time ranging between 0.25 to 3 years, depending on the subject tissue, its location in the human body, its mechanical properties, and the functional requirements associated with the adhesive-repaired site. Recognizing the outstanding properties of cyanoacrylates as tissue adhesive, sealants, and blocking agents, and the existing need to repair different biological tissues having a broad range of mechanical properties and healing profiles, evoked the need to develop new cyanoacrylate formulations to meet such requirements. The present invention provides novel 2-cyanoacrylate formulations with the sought properties.

SUMMARY OF THE INVENTION

In one aspect, the present invention is directed to a bioabsorbable adhesive formulation which is an admixture of 2-alkoxyalkylcyanoacrylate and an oxalate polymer of polyethylene glycol, wherein the polyethylene glycol has an average degree of polymerization of more than 4. Preferably, the polyethylene glycol is simultaneously polymerized with an oxalate monomer in the presence of an alkane diol. It is also preferred that the admixture further contains poly(2-alkoxyalkylcyanoacrylate). It is also within the scope of the present invention that the oxalate polymer of polyethylene glycol is a copolymer of polyethylene glycol oxalate and trimethylene carbonate. Furthermore, it is also within the scope of the present invention that the oxalate polymer of polyethylene glycol is a copolymer of polyethylene glycol oxalate and trimethylene succinate. It is preferred that the 2-alkoxyalkylcyanoacrylate is 2-methoxypropylcyanoacrylate.

In another aspect, the present invention is directed to a bioabsorbable adhesive formulation which is an admixture of 2-alkoxyalkylcyanoacrylate and a trimethylene carbonate-based polymer. Preferably, the trimethylene carbonate-based polymer is made using a polyfunctional initiator such as trimethylolethane, trimethylolpropane, pentaerythritol or glycerol.

Optionally, the trimethylene carbonate-based polymer may be a homopolymer or the trimethylene carbonate-based polymer may be a copolymer of trimethylene carbonate and one or more cyclic esters such as glycolide, lactide, p-dioxanone, ε-caprolactone, and 1,5-dioxepan-2-one. It is preferred that the 2-alkoxyalkylcyanoacrylate is 2-methoxypropylcyanoacrylate.

In yet another aspect, the present invention is directed to a bioabsorbable adhesive formulation which an admixture of 2-alkoxyalkylcyanoacrylate and a vinyl acetate-based polymer, wherein the 2-alkoxyalkylcyanoacrylate is preferably 2-methoxypropylcyanoacrylate.

In a still further aspect, the present invention is directed to a bioabsorbable adhesive formulation which is an admixture of 2-alkoxyalkylcyanoacrylate and a polytrimethylene dicarboxylate of a diacid such as succinic acid, glutaric acid, and adipic acid. Preferably, the polytrimethylene dicarboxylate of a diacid is further grafted with one or more cyclic monomers such as trimethylene carbonate, glycolide, lactide, p-dioxanone, ε-caprolactone, and 1,5-dioxepan-2-one. It is preferred that the 2-alkoxyalkylcyanoacrylate is 2-methoxypropylcyanoacrylate.

In a still further aspect, the present invention is directed to a bioabsorbable adhesive formulation comprising an admixture of 2-alkoxyalkylcyanoacrylate and a low melting crystalline copolymer such as ε-caprolactone, glycolide, and lactide, wherein the 2-alkoxyalkylcyanoacrylate is preferably 2-methoxypropylcyanoacrylate.

Preferably, the bioabsorbable adhesive formulation of the present invention is used in adjoining severed or mechanically compromised organs or tissues or in sealing mechanically compromised tissues. Another preferred application for the present adhesive formulation is as a hemostatic agent at bleeding sites. For such application the present adhesive formulation may optionally be combined with one or more organic or inorganic salts of a multivalent metal such as those of calcium, zinc, and iron. A most preferred inorganic salt is ferric chloride.

It is also within the scope of the present invention that the present adhesive formulation may be combined with a chitosan-based pledget. Preferably, such pledget is made of 70–90 percent deacetylated chitin. In a preferred method of application the pledget is precoated on both sides with the present inventive adhesive formulation prior to its use in adjoining two surfaces. Preferably such precoated pledget is used in combination with the hemostatic agent which is a blend of the present adhesive formulation and ferric chloride. For such method of application, the pledget is lightly pressed at the compromised site shortly after applying the hemostatic formulation.

It is also within the scope of the present invention that the present bioabsorbable adhesive formulation includes an organic dye such as D&C violet #2.

Also within the scope of the present invention is a method for patching or adjoining different body organs or tissues using a combination of an elastin patch and the present inventive adhesive formulation, wherein the adhesive is employed at the interface between the elastin and biological site. Such method is appropriate for the anastomosis or patching of compromised sites in the gastrointestinal tract, urinogenital system, respiratory system, or cardiovascular system.

DESCRIPTION OF THE PREFERRED EMBODIMENTS

This invention deals with novel tissue adhesive formulations based on combinations of a 2-cyanoacrylate ester and one or more compliant, absorbable polyesters (or similar chemical entities), including slow-absorbing ones or a combination of both types of polyesters. More specifically, the cyanoacrylate fraction of these formulations comprises at least one 2-cyanoacrylate ester of the general formula I.

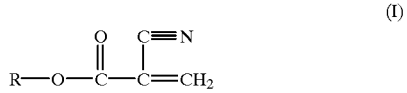

(I)

wherein R is selected from the group consisting of alkyl groups having from 1 to about 8 carbon atoms and, preferably, alkoxyalkyl groups having the formula $R_1$—O—$R_2$ wherein $R_1$ is an alkyl group having from 1 to about 8, preferably 2 to 3 carbon atoms and $R_2$ is an alkylene group having from 3 to about 6, preferably 3 to 4 carbon atoms. The polyester component can be admixed with the cyanoacrylate component at a level of about 2 to 50 percent, preferably 2 to 25 percent and more preferably from about 5 to 10 percent. The polyester component comprise one or more of the following types of polyesters: (1) polyalkylene succinate, preferably polytrimethylene succinate; (2) copolymers of a polyalkylene succinate and trimethylene carbonate; (3) polyalkylene succinate grafted with one or more of the following monomers: trimethylene carbonate, lactide, glycolide, ε-caprolactone, 1,5-dioxepan-2-one, and p-dioxanone; (4) copolyesters of a polyalkylene oxalate and trimethylene carbonate; (5) copolyester of oxalate polymer and trimethylene carbonate wherein the oxalate functionalities are linked to polyethylene polyglycol having a Mn in excess of 200 Da; (6) copolyesters of polytrimethylene succinate and an alkylene oxalate; (7) copolyesters of an oxalate polymer of trimethylene diol or polyethylene glycol and a polyalkylene succinate; (8) a copolyester comprising a polyethylene glycol linked to succinate and oxalate units; (9) an oxalate polymer of a polyethylene glycol having an average degree of polymerization of more than 4; (10) an oxalate copolymer of a polyethylene glycol having a degree of polymerization of more than 4 and an alkane-diol; (11) a polytrimethylene carbonate; (12) a copolymer of trimethylene carbonate and one or more cyclic ester such as glycolide, lactide, ε-caprolactone, morpholinedione, and p-dioxanones; (13) a vinylacetate-based polymer; (14) a block copolymer of polyethylene glycol and one or more cyclic monomers such as trimethylene carbonate, glycolide, lactide, ε-caprolactone, morpholinedione, and p-dioxanone; (15) polytrimethylene dicarboxylate of acids such as succinic, glutaric, and adipic acids; (16) a copolymer of a polyalkylene succinate and trimethylene carbonate; (17) a polyalkylene dicarboxylate grafted with one or more cyclic monomer such as trimethylene carbonate, glycolide, lactide, p-dioxanone, ε-caprolactone, and 1,5-dioxepan-2-one; (18) a copolymer of a polyethylene glycol oxalate and trimethylene carbonate; (19) a copolyester of trimethylene succinate and alkylene oxalate; and (20) a low melting crystalline copolymer of ε-caprolactone, glycolide, and dl-lactide.

Another aspect of this invention deals with crystalline absorbable materials made of segmented or block copolymers, wherein the crystalline fraction is due to segments or blocks that melt below 70° C. and the entire system displays a $T_g$ below 50° C. More specifically, this invention deals with two types of crystalline copolymers, wherein the crystalline fraction is due to polyalkylene oxalate or caprolactone-based segment/blocks. A preferred composition of this invention is a copolymer made by end-grafting one or two cyclic monomers onto a crystalline copolymeric alkylene oxalate chain. In a more preferable embodiment, the alkylene oxalate chains are based on randomly placed units of hexamethylene and octamethylene oxalate end-grafted with dl-lactide or a mixture of dl-lactide and glycolide to produce a crystalline polyalkylene oxalate fraction and an amorphous poly-2-hydroxy acid fraction. In turn, this amorphous fraction can be made from dl-lactide and/or one or more monomer such as p-dioxanone, caprolactone, glycolide, and trimethylene carbonate. This invention also deals with crystalline copolymers with a crystalline fraction derived from an ε-caprolactone-based segment/block and a non-crystalline faction due to segments/blocks formed by subsequent copolymerization of the crystalline component with dl-lactide and/or one or a mixture of cyclic monomers such as p-dioxanone, ε-caprolactone, glycolide, and trimethylene carbonate. A preferred composition of this copolymer is made in two steps. In the first step 90/10 copolymeric chain of ε-caprolactone and glycolide is formed by ring opening polymerization. In the second step, the resulting crystalline product is then grafted with dl-lactide and glycolide in an approximately 65/52 ratio. These compositions can be converted to compliant films having a tensile modulus of less than 300,000 psi which can be used as a barrier or part of a composite system for use for post-surgical adhesion prevention. Most important is the use of these copolymers as high molecular weight compositions (having an inherent viscosity of more than 0.4 in hexafluoro isopropyl alcohol) as a modifier to a fast-polymerizing cyanoacrylate tissue adhesive/sealant, such as those based on methoxypropyl cyanoacrylate (MPC) to form adhesive coherent materials which display higher compliance than systems devoid of the modifier subject of this invention.

Another aspect of this invention deals with a unique formulation comprising an absorbable 2-cyanoacrylate and a polyester at a ratio between 95/5 and 50/50 wherein the polyester is one or more of those described above. In another aspect of this invention, the subject formulation can be used in repairing or sealing soft tissues including, but not limited to, those of the skin and all internal tissues such as those of the cardiovascular, digestive, ocular, urinogenital and respiratory systems, muscles, tendons, ligaments and articulating cartilaginous components. Another aspect of this invention is the use of these formulations, with and without an inorganic or organic metallic additive, as hemostatic agents. Preferably, such additives are inorganic and/or organic salts of iron, such as ferric chloride, ferric citrate, and ferric gluconate. Another aspect of this invention is the use of the subject formulation in attaching natural or synthetic patches used in repairing defective walls, as in repairing the retina, abdominal wall and conduits of the respiratory, vascular, and urinogenital systems. Another aspect of this invention is a formulation of an absorbable cyanoacrylate and polyester that can be used with or without an antimicrobial agent as a cover for open wounds, burns, and ulcers.

Another aspect of this invention deals with a hemostatic adhesive formulation comprising an absorbable crystalline microparticulate cation exchanger with or without an immobilized metal ion such as $Fe^{+2}$, $Fe^{+3}$, $Ca^{+2}$, $Mg^{+2}$, and $Zn^{+2}$. The microparticles can be dispersed in a absorbable liquid gel-former, a liquid copolyester, or polytrimethylene carbonate, which may also be mixed with a cyanoacrylate monomer such as MPC.

Another aspect of this invention deals with a hemostatic formulation comprising an absorbable cyanoacrylate such as an the alkoxyalkyl cyanoacrylate admixed with polymeric oxalates, as modifiers, which have been patented as hemostatic agents that form compliant films that undergo absorption in the biologic environment (U.S. Pat. No. 5,350,798). Known absorbable and non-absorbable cyanoacrylates affect hemostasis through rapid conversion to a polymeric barrier which physically interrupts bleeding at the application site. Occasionally, these barriers fail at sites experiencing pulsatile stresses as in the case of punctured blood vessels. This provided an incentive to explore new cyanoacrylate formulations that have the acknowledged attributes of the physical barriers but interact directly with the blood components to maximize the hemostatic effect without compromising the safety of the system. Hence, this invention deals with cyanoacrylate formulations containing polymeric modifiers for controlling their viscosity and/or absorption, in addition to miscible iron salts that can themselves contribute to the hemostatic events. And this invention deals more specifically with an absorbable cyanoacrylate formulation containing at least one polymeric modifier for increasing the compliance or the absorption rate of the resulting polycyanoacrylate and a miscible iron salt for enhanced hemostatic effect. Thus, one aspect of the invention deals with an absorbable formulation of an alkoxyalkyl cyanoacrylate with at least one absorbable modifier capable of increasing the polycyanoacrylate compliance and its absorption rate and a miscible iron salt for increasing the hemostatic efficiency, wherein the polymeric modifiers are (1) oxalate polymers of oligomeric ethylene glycol or polyethylene glycol (PEG); (2) copolyesters of trimethylene carbonate/glycolide, a mixture of trimethylene carbonate, caprolactone and glycolide, or a mixture of lactide glycolide and ϵ-caprolactone; and (3) acid tipped polyethylene glycol, copolyesters of "2" or their copolymers with PEG. The iron salt can be a ferric chloride or iron salt of gluconic or citric acid. Another aspect of this invention describes the use of a slow-absorbing cyanoacrylate formulation based on an alkyl cyanoacrylate and one or more polymeric modifiers capable of increasing the compliance of the polyalkyl cyanoacrylate, wherein said modifier comprises a copolyester having one or more of the chain repeat units: trimethylene succinate, trimethylene carbonate, and ϵ-caprolactone, which may be covalently attached to PEG segments. Similar low modulus, practically amorphous or liquid linear or branched polyesters or vinyl acetate-based polymers can be used as modifiers. Typical vinyl acetate-based polymers are polyvinyl acetate and 5/95 or 25/75 ethylene vinyl acetate copolymers. Another aspect of this invention is the use of a thin film or pledget comprising a chitosan or an acylated chitosan to aid the performance of the liquid formulation and accelerate the hemostatic effect.

In another aspect of this invention, the polymeric modifier is an acylated chitosan. In another aspect of this invention, the polymeric modifier is liquid at room temperature. In another aspect of the invention, the polymeric modifier represents at least 1–50% of the mass of the alkoxyalkyl cyanoacrylate-based formulation. In another aspect of this invention, the polymeric modifier is a polyester of polyethylene glycol and one or more of the following diacids, adipic acid, succinic, and glutaric acid. In another aspect of the invention, polymeric alkoxyalkyl cyanoacrylates having a molecular weight of at least 1000 Dalton can be the modifier or part of a mixture of polymeric modifiers. In another aspect of the invention, the polymeric modifier is a mixture of two or more systems, one of which is a high molecular polymer of an alkoxyalkyl cyanoacrylate.

In another aspect of this invention, the performance of the adhesive or hemostatic adhesive can be aided by using a chitosan-based pledget as an adjuvant that facilitates the positioning of said adhesive or hemostatic adhesive and accentuate the hemostatic effect of the latter. The pledget can be prepared by extruding a solution of chitosan (made preferably by 70–90% deacetylation of the acetamido groups of chitin) acetate into an alkaline coagulating bath to produce thin films. These can be pressed and cut into proper sizes to produce the pledget subject of this invention. In yet another aspect of the invention, a pledget similar to the chitosan-based one comprising a partially or fully denatured protein film, which may also contain a multivalent metal ion such as $Fe^{+3}$, is used to accentuate the hemostatic effect of the liquid formulation. The protein may or may not be acylated with a cyclic anhydride such as glutaric anhydride. The protein can be albumin or a soy protein isolate.

Typical examples of the absorbable formulations and their performance are given below, which are comprised of methoxypropyl cyanoacrylate (MPC), a lactide/glycolide/ϵ-caprolactone copolymeric modifier (L1) and polymethoxypropyl cyanoacrylate (MPC) that is formed by the free radical polymerization of MPC. Specific examples for the preparation of representative adhesive formulations and their use as components in hemostatic/adhesive systems and their intermediates are also illustrated below.

EXAMPLE 1

Preparation and Characterization of a Copolymer of Caprolactone, dl-Lactide and Glycolide First, a prepolymer of 90/10 ϵ-caprolactone/glycolide copolymer was prepared using decyl alcohol as the initiator and stannous octoate as the catalyst, respectively. The polymerization was conducted at 170° C. The resulting polymer was cooled to 120° C. and a 65/52 mixture of glycolide and dl-lactide added. When the added monomers dissolved with stirring at about 120° C., the second stage of the polymerization process was then completed at about 170° C. Trace amounts of unreacted monomer were distilled under reduced pressure at about 110° C. The resulting product was shown by DSC to melt at about 48° C. and underwent a glass transition below 40° C. The polymer was shown to have an inherent viscosity of 0.35 in chloroform at 0.1 percent concentration.

EXAMPLE 2

Preparation of a 96/4 ϵ-Caprolactone/Glycolide Copolymer

Glycolide (0.08865 moles) was mixed with ϵ-caprolactone (1.455 moles) and a catalytic amount of stannous octoate (0.3 moles) and tartaric acid (0.075 moles). The system was heated at 150° C. and was stirred at this temperature for 6 hours. At the conclusion of the reaction, the unreacted monomer was removed by heating at 120° C. under reduced pressure for 30 minutes. The resulting polymer had a peak melting temperature of 49.1° C. as measured by DSC and an $M_w$ of 151,948 as measured by GPC.

EXAMPLE 3

Preparation of a 95/5 ϵ-Caprolactone/Glycolide Copolymer

Glycolide (0.21 moles) was mixed with ϵ-caprolactone (4.0 moles) and a catalytic amount of stannous octoate (0.8 mole) and glycolic acid (0.40 moles). The system was heated to 150° C. and was stirred at this temperature for 14 hours. At the conclusion of the reaction, the unreacted monomer was removed by heating at 120° C. under reduced pressure for 1 hour. The resulting polymer had a peak melting temperature of 54.3° C. as measured by DSC.

EXAMPLE 4

Preparation of a (ε-Caprolactone-Glycolide)/ (Lactide-Glycolide) Copolymer

Glycolide (0.13 moles) was mixed with ε-caprolactone (1.18) and a catalytic amount of stannous octoate (0.262 mole) and 1-decanol (3.275 mole). The system was heated to 170° C. and was stirred at this temperature for 30 minutes. The reaction was then cooled to 120° C. Glycolide (0.65 moles) and dl-lactide (0.52 moles) were added to the prepolymer. After melting the second charge, the system was heated to 170° C. and was stirred at this temperature for 6.5 hours. At the conclusion of the reaction, the unreacted monomer was removed by heating at 130° C. under reduced pressure for 1.5 hours. The resulting polymer was characterized by DSC (for $T_m$), solution viscosity (for molecular dimensions), IR and NMR (for chemical composition).

EXAMPLES 5 through 7

Preparation of 95/5 (by weight) Methoxy Propyl Cyanoacrylate/Modifier Adhesive Formulations The adhesive formulations of Examples 5–7 were prepared by dissolving 5% (by weight) modifier in 95% methoxy propyl cyanoacrylate (MPC). Components were measured in a 15 ml polypropylene centrifuge tube. The modifier was dissolved at ambient temperature by shaking and vortexing over the course of several hours. After extended mixing periods, the modifier dissolved in the MPC and formed a one-phase solution.

TABLE I

Adhesive Plasticizer Formulations

| Example No. | Modifier of Example No. |
|---|---|
| 5 | 1 |
| 6 | 2 |
| 7 | 3 |

EXAMPLE 8

Preparation of 90/10 Methoxy Propyl Cyanoacrylate/Modifier Adhesive Formulation

This adhesive formulation was prepared by dissolving the modifier of Example 1 in MPC at a 10/90 weight ratio. Components were mixed in a 15 ml polypropylene centrifuge tube. The plasticizer was dissolved at ambient temperature by shaking and vortexing over the course of several hours. After extended mixing periods, the plasticizer dissolved in the MPC and formed a one phase liquid solution.

EXAMPLES 9 and 10

Dye Addition to Adhesive Formulations

D and C violet #2 was added to the formulations of Example Nos. 5 and 8 at a concentration of 0.05% (by weight). The dye was measured into the already prepared formulations and was dissolved by shaking and vortexing at room temperature. The resulting material was a one phase liquid solution.

EXAMPLES 11 through 14

In Vitro Bond Strength Evaluation of Adhesive Formulations Using Goat Skin

A layer of paraffin wax approximately 2 cm thick was molded into the bottom of 15 cm×26.5 cm polypropylene containers. Goat skin (7.5 cm×20.5 cm) was dissected from the subcutaneous tissue, stretched to its original dimensions, and pinned onto the wax. Each skin sample was then submerged in a saline solution (0.9% w/vol. NaCl and 0.05% w/vol. $NaN_3$). Samples were stored in a freezer at −10° C.

Prior to use, each sample was removed from the freezer and thawed. Saline was decanted from the container, and the skin was rinsed with cold water. All excess moisture was decanted, and the sample was blotted dry. Two 19 cm incisions were cut along the length of the skin sample. The skin about the incision was approximated and 400 μL of an adhesive formulation was applied. After polymerization, each incision was cut into test strips approximately 2 cm wide. The samples were tested in tension on an MTS 858 Minibionix universal testing apparatus at a strain rate of 0.42 mm/sec. The wound strength was calculated as the force required to separate the adjoined ends of the incision divided by the cross sectional area of the sample. The average wound strength for each formulation and the corresponding standard deviation are presented in Table II.

TABLE II

Adhesive Strength Data

| Example | Formulation | Strength (kPa) |
|---|---|---|
| 11 | 100% MPC* | 123 ± 43 |
| 12 | Ex. No. 5 | 150 ± 30 |
| 13 | Ex. No. 6 | 100 ± 27 |
| 14 | Ex. No. 7 | 74 ± 35 |

*as a comparative example

EXAMPLES 15 and 16

In Vivo Performance of Adhesive Formulations

The tissue adhesive formulation of Example No. 5 and, for comparative purposes, 100% MPC, were tested using an in vivo model in Sprague Dawley rats that weighed approximately 225 g. Anesthesia was induced via subcutaneous injection of 0.5 mg/kg acepromazine and 0.05 mg/kg buprenorphine; rats were maintained under anesthesia via 1.5–2.5% isofluorane inhalation. Once anesthetized, rats were shaved and scrubbed with Nolvasan scrub. Four incisions were made on the back of each rat. Two incisions were made 2 cm lateral to the dorsal midline on each side of the rat. Each incision was approximately 4 cm long and 1 cm separated each incision on each side of the rat. Several incisions were selected as controls and closed with four interrupted sutures (Vicryl Size 3–0 braided suture, Ethicon). Remaining incisions were approximated and 75 μL F-65 was applied. Rats were fitted with Elizabethan collars to minimize interference with the incisions.

At two weeks post-op, rats were euthanized in a $CO_2$ precharged chamber. The skin from the back of each rat was dissected from the subcutaneous tissue. Each incision was cut into two test strips approximately 1 cm wide. Healed incision strength was measured in tension using an MTS 858 Minibionix at a strain rate of 0.42 mm/sec. The wound breaking strength was calculated as the force required to separate the wound divided by the cross sectional area of the sample. The average wound strength for each set and the corresponding standard deviation are presented in Table III. The breaking strength of the healed incisions was comparable to those augmented with sutures. Each average and standard deviation in the table is based on at least eight separate repaired incisions.

TABLE III

In vivo Performance

| Example | Formulation | Wound Strength, kPa |
|---|---|---|
| 15 | 100% MPC | 633 ± 116 |
| 16 | Ex. No. 5 | 683 ± 232 |

EXAMPLE 17

Ferric Chloride and Ferrous Gluconate Hemostatic Formulations

To enhance the hemostatic properties of the adhesive formulation of Example 5, it was mixed with 5% (by weight) of ferric chloride to form a uniform solution. In addition, both ferric chloride and ferrous gluconate were mixed with the adhesive formulation of Example 8 at amounts ranging from 0.1% to 10% (by weight). The ferric chloride and ferrous gluconate were dissolved by shaking and vortexing at room temperature.

EXAMPLE 18

Preparation of Limited Hydrophilicity Modifier

A low hydrophilicity copolymer of polyethylene glycol 400 (PEG-400) with trimethylene carbonate (TMC) and glycolide was prepared by grafting 15 parts of PEG-400 with 85 parts of TMC following the general procedure of U.S. Pat. No. 5,612,052.

EXAMPLES 19–21

Preparation of Typical Hemostatic/Adhesive Formulations for In Vitro And Evaluation Methoxypropyl cyanoacrylate was mixed with the desired modifier (which has been sterilized at 120° C. for 1 hour) in a laminar flow hood and then agitated to produce a visually One-phase system. The formulations are given below in Table IV.

TABLE IV

Composition of Components of Key Hemostatic Adhesive Formulations

| Example | Composition |
|---|---|
| 19 | 95/15 MPC/Modifier of Example 4 |
| 20 | 90/10 MPC/Modifier of Example 18 |
| 21 | 85/15 MPC/Modifier of Example 18 |

EXAMPLES 22through27

In Vitro Evaluation of Gel-Forming Adhesive Formulations for Blood Clotting

Heparinized blood samples were collected from a New Zealand white rabbit. The clotting potential of adhesive formulations was tested by adding 100 µL of blood and 10 µL of the adhesive formulation to a well in a 96 well microtiter plate. Ten such samples were tested per formulation. The samples were visually inspected over the course of 30 min. and observations were recorded. The formulations were rated as poor, moderate, or good blood clotters as shown in Table V.

TABLE V

In Vitro Blood Clotting Performance

| Example | Formulation | Heparinized Blood |
|---|---|---|
| 22 | 5% FeCl$_3$ in form. of Ex. 5 | Not Tested |
| 23 | 5% FeCl$_3$ in form. of Ex. 19 | Good |
| 24 | 2.0% FeCl$_3$ in form. of Ex. 8 | Moderate |
| 25 | 5.0% FeCl$_3$ in form. of Ex. 8 | Moderate |
| 26 | 10.0% FeCl$_3$ in form. of Ex. 8 | Good |
| 27 | 3.0% ferrous gluconate in formulation of Ex. 8 | Good |
| 28 | 4.0% ferrous gluconate in formulation of Ex. 8 | Moderate |

EXAMPLES 29through32

In Vivo Evaluation of Formulations Using the Liver Incision Test for Blood clotting Efficiency Twelve-week-old New Zealand white rabbits were anesthetized via 2% isofluorane inhalation. The rabbits were shaved and scrubbed, then incised to expose the liver. An incision was cut into the liver measuring 2 cm in length. Several microliters of adhesives outlined in Examples 22–25 were applied to the wound, and the hemostatic properties of each formulation was observed as recorded in Table VI.

TABLE VI

Liver Incision Clotting Performance

| Example | Formulation Example No. | Observations |
|---|---|---|
| 29 | 22 | Bleeding stopped immediately upon application. |
| 30 | 23 | Bleeding stopped immediately. |
| 31 | 24 | Bleeding stopped initially but wound reopened. |
| 32 | 25 | Incision bled from underneath adhesive. |

EXAMPLE 33

In Vivo Evaluation of Formulation Using the Vena Cava Puncture Test for Blood Clotting Efficiency after the liver incision tests detailed in Examples 29–32 were completed, the vena cava was exposed and a small puncture wound was created perpendicular to the length of the vessel. Adhesive formulations made in accordance with Example Nos. 22 and 26 were applied to the wound, finger pressure was applied to the site, and the bleeding ceased immediately.

EXAMPLE 34

In Vivo Evaluation of Absorbable Hemostatic Formulation

A New Zealand white rabbit was anesthetized and a midline incision was made starting at the xiphoid process and extending 12 cm to a point caudal to the umbilicus. The peritoneum was entered and the liver was isolated. A 2 cm long incision was made on the liver and either 100 ul of a hemostatic formulation or the hemostatic formulation soaked into a chitosan pledget was applied to the wound. In addition, a piece of chitosan pledget (thin film made by casting a base-coagulated chitosan acetate solution) was tested alone as a control. The formulation of Example 23 was applied using sterile tips and a micropipette. Observations on the hemostatic properties of the material were recorded along with the time to stop bleeding (where possible).

The formulation of Example 23 was also tested on a vena cava puncture wound. In addition, a piece of chitosan pledget was tested alone as a control. The vena cava was exposed and punctured with an 18 gauge needle. The hemostatic formulation (~100 µl) was applied to the chitosan pledget, placed on the wound, and then general observations on the hemostatic property were recorded.

Example 35

General Procedure for Preparation of Carboxy-Terminated Copolyester

The present liquid copolyester was made by ring-opening a mixture of 95/5 trimethylene carbonate/glycolide with ethylene glycol as an initiator and stannous octoate as a catalyst at 160° C. for 1.5 hours. Typically, the liquid polymer, which is hydroxy-terminated, is treated with an equivalent amount of glutaric anhydride to esterify the end-groups and form carboxylic groups at both ends of the chain. The reaction is carried out by heating the mixture at about 100° C. for 30 min., 110° C. for 40 min, then at 120° C. for 40 min. The product is then heated under reduced pressure (about 0.1 mm Hg) at 120° C. to remove traces of unreacted anhydride. For specific examples, the presence of carboxylic end-groups was confirmed by titration in conjunction with IR spectroscopy and GPC (for determining molecular weight and molecular weight distribution).

Example 36

Adhesive Formulation Based on a Carboxy-Terminated Copolyester

A 90/10 mixture of MPC and a carboxy-terminated copolyester made in accordance with Example 35, with and without 1% chopped (1 mm length) polyglycolide yarn, was prepared and the adhesive properties of the formulation with and without the yarn were evaluated in vitro. Results indicate the carboxylation as well as the chopped fibers contribute significantly to ease of application and eventual bond strength, respectively. The chopped fibers accelerated blood clotting.

Example 37

Breaking Strength of Repaired Skin Wounds

As part of the animal protocol, anesthesia was induced via subcutaneous injection of 0.5 mg/kg acepromazine and 0.05 mg/kg buprenorphine. Rats were maintained under anesthesia via 1.5–2.5% isofluorane inhalation. Once anesthetized, rats were shaved and scrubbed with Nolvasan scrub. Four incisions were made on the back of each rat. Two incisions were made 2 cm lateral to the dorsal midline on each side of the rat. Each incision was approximately 4 cm long and 1 cm separated each incision on each side of the rat. The incisions on the left side were used as controls; these were closed with either four surgical staples or four interrupted sutures. The incisions on the right side were closed with an adhesive formulation; a limited number of these also received two surgical staples to insure wound closure.

At two weeks post-operative, rats were euthanized in a $CO_2$ precharged chamber. The back skin from the rats was dissected from the subcutaneous tissue. Each incision was cut into two test strips approximately 1 cm wide. Healed incision strength was measured in tension using an MTS 858 Minibionix at a strain rate of 0.42 mm/sec. The wound strength was calculated as the force required to separate the wound divided by the cross sectional area of the sample. The average wound strength for each set and the corresponding standard deviation are presented in Table VII. Each average and standard deviation in the table is a result of at least eight separate incisions.

TABLE VII

In Vivo Wound Strength Data

| Set | Left Incision* | | Right Incision | |
|---|---|---|---|---|
| | Means to Edge Approximation | Wound Strength (KPa) | Means to Edge Approximation | Wound Strength (KPa) |
| 1 | 4 staples | 437 ± 97 | Form. of Ex. 20 | 546 ± 262 |
| 2 | 4 sutures | 631 ± 158 | Form. of Ex. 20 | 622 ± 141 |
| 3 | 4 staples | 435 ± 238 | Form. of Ex. 20 and 2 staples | 395 ± 172 |

*Control incision.

The foregoing description of preferred embodiments of the invention has been presented for illustration, and is not intended to be exhaustive. Modifications are possible in light of the above teachings or may be acquired from practice of the invention.

What is claimed is:

1. A bioabsorbable adhesive formulation comprising an admixture of 2-alkoxyalkylcyanoacrylate and a trimethylene carbonate-based polymer.

2. The bioabsorbable adhesive formulation set forth in claim 1 wherein the trimethylene carbonate-based polymer comprises a homopolymer.

3. The bioabsorbable adhesive formulation set forth in claim 1 wherein the trimethylene carbonate-based polymer comprises a copolymer of trimethylene carbonate and one or more cyclic esters selected from the group consisting essentially of glycolide, lactide, p-dioxanone, ε-caprolactone, and 1,5-dioxepan-2-one.

4. The bioabsorbable adhesive formulation set forth in claim 1 wherein the 2-alkoxyalkylcyanoacrylate comprises 2-methoxypropylcyanoacrylate.

* * * * *